United States Patent [19]
Danks et al.

[11] Patent Number: 6,159,223
[45] Date of Patent: Dec. 12, 2000

[54] SURGICAL CLIP APPLICATOR

[75] Inventors: John K. Danks, Delray Beach, Fla.; Jeffrey A. Wilson, Mendon, Mass.

[73] Assignee: Endoscopic Concepts, Inc., Del Ray Beach, Fla.

[21] Appl. No.: 09/312,453

[22] Filed: May 14, 1999

Related U.S. Application Data

[60] Provisional application No. 60/117,325, Jan. 26, 1999.

[51] Int. Cl.[7] ................................................ A61B 17/12
[52] U.S. Cl. ............................................................ 606/142
[58] Field of Search ................................... 606/142–144, 606/139, 143, 219; 604/95, 171, 280

[56] References Cited

U.S. PATENT DOCUMENTS

| | | |
|---|---|---|
| 4,418,694 | 12/1983 | Beroff et al. |
| 4,476,865 | 10/1984 | Failla et al. |
| 4,572,181 | 2/1986 | Mattler ................................. 606/142 |
| 4,616,651 | 10/1986 | Golden ................................. 606/142 |
| 5,030,226 | 7/1991 | Green et al. ......................... 606/158 |
| 5,163,945 | 11/1992 | Ortiz ..................................... 606/142 |
| 5,171,249 | 12/1992 | Stephanchik et al. .............. 606/142 |
| 5,439,468 | 8/1995 | Schulze et al. ..................... 606/143 |
| 5,601,573 | 2/1997 | Fogelberg et al. .................. 606/143 |

*Primary Examiner*—Michael Buiz
*Assistant Examiner*—(Vikki) Hoa B. Trinh
*Attorney, Agent, or Firm*—Miller & Martin LLP

[57] ABSTRACT

A method and apparatus for ligating tissue is disclosed. The applicator utilizes a jaw portion having jaw members with jaw faces to grasp tissue and operating portions to apply a surgical clip. In a presently preferred embodiment, the surgical clip utilized is a self-closing clip. Operating faces in the operating portion of the jaw members separate the clip from the tissue prior to clip installation. The applicator has a channel in the operating portion for user viewing which also may allow for lateral displacement of a clip external to the jaw faces.

25 Claims, 3 Drawing Sheets

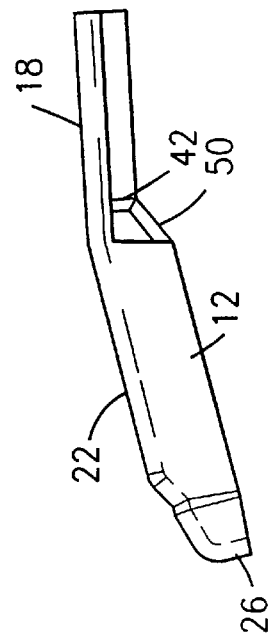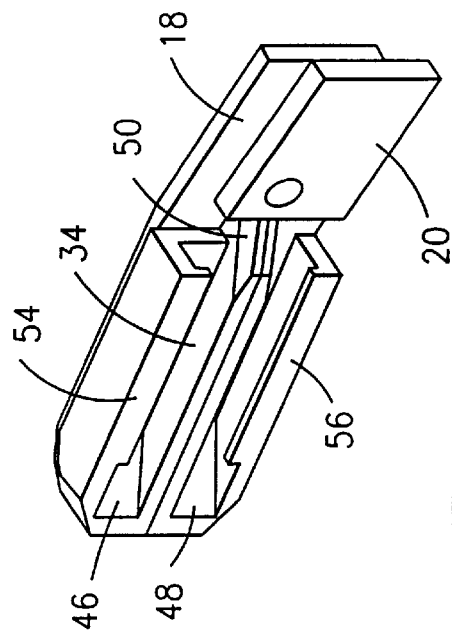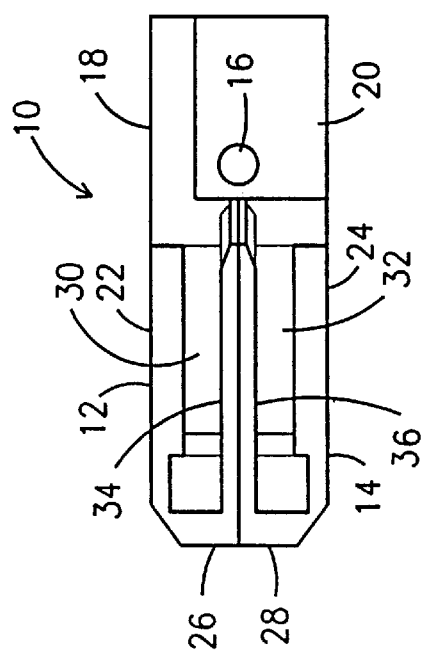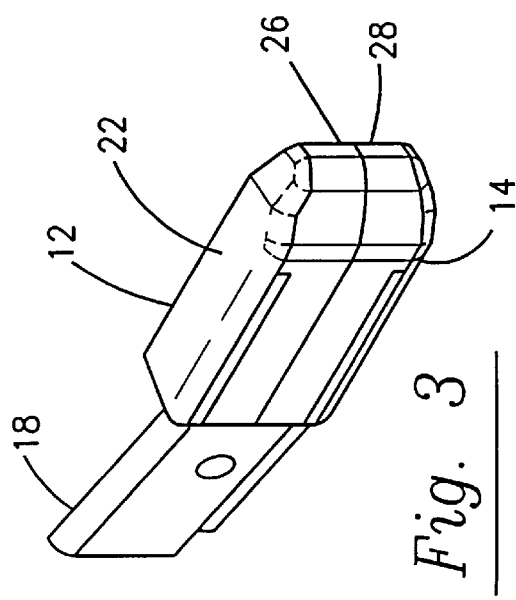

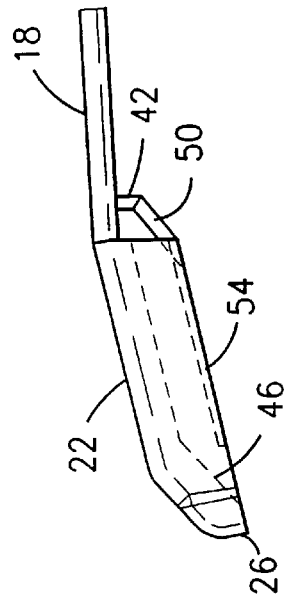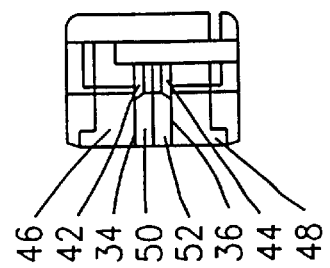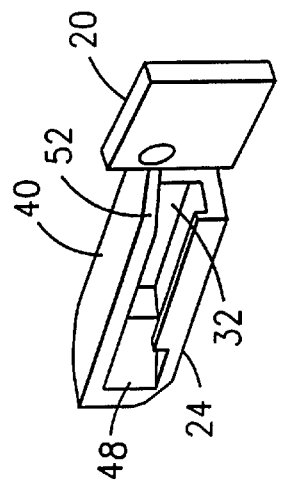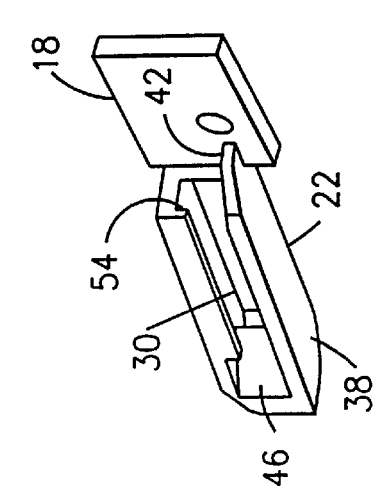
Fig. 5
Fig. 6
Fig. 7
Fig. 8

SURGICAL CLIP APPLICATOR

The present invention claims priority to U.S. Provisional Patent Application Ser. No. 60/117,325 filed Jan. 26, 1999.

BACKGROUND OF THE INVENTION

1. Field of the Invention

The present invention relates generally to devices which are utilized to apply surgical clips and, more particularly, to such devices having a jaw capable of receiving tissue and applying a self-closing clip adapted to replace a suture knot during laparoscopic or endoscopic surgery.

2. Description of Related Art

As medical and hospital costs continue to increase, surgeons are constantly striving to develop advanced surgical techniques. Advances in the surgical field are often related to the development of operative techniques that involve less invasive surgical procedures and reduce overall patient trauma. In this manner, the length of hospital stays and patient recovery can be significantly reduced, and therefore hospital and medical costs can be reduced as well.

Suturing is a procedure that surgeons are required to perform to repair or reconstruct traumatized body tissue. Medical instruments have been recently designed to allow a surgeon to manipulate a suture, or suture and needle combination, through the small diameter opening of a cannula. However, the ability to tie an appropriately placed suture may be problemsome in certain confined spaces.

One advance in recent years to reduce the evasiveness of surgical procedures is endoscopic surgery. Endoscopic surgery involves the use of an endoscope, which is an instrument permitting the visual inspection and magnification of a body cavity. The endoscope is inserted through a cannula after puncture through a wall of the body cavity with a trocar assembly that includes a sharp-pointed obturator interfitting in the cannula. After removing the obturator, the surgeon can perform diagnostic and therapeutic procedures at the surgical site with the aid of specialized instrumentation designed to fit through additional the cannula. Fore some procedures, multiple trocars providing small diameter openings into the desired body cavity may be required.

Increased versatility of endoscopic staple and clip applying mechanisms enhance the effectiveness of endoscopic procedures. These mechanisms are placed through a cannula of an endoscopic trocar so that the tissue may be cut, stapled or ligated. With the advent of these devices, however, there have been certain noted inadequacies. Many of these inadequacies have become perceived solely because of the newness of the endoscopic procedures.

It is known in the art to use hemostatic clips and clip appliers to ligate blood vessels and other tubular members. Such hemostatic clips and clip appliers are described, for example, in U.S. Pat. Nos. 4,418,694, 4,476,865, 5,030,226, 5,163,945, 5,171,249, and 5,439,468. In performing a ligating procedure with these types of clip appliers, the jaws physically deform a clip about a vessel or tissue to be clamped or ligated.

Additionally, the use of a surgical clip applier combined with a special self-closing surgical clip has been demonstrated in U.S. Pat. No. 5,601,573. However, the surgical clips utilized by this clip applying device must have special tabs which cooperate with special rails and special shelves within the jaws of the device in order to separate the special self-closing surgical clip. This instrument does not allow the operator to view the clip while deploying it to a desired location.

In view of the deficiencies of the prior art for creating a useful endoscopic alternative to tying a suture knot, what is desired within the medical community is a device suitable for application using endoscopic techniques to successfully replace the suture knot. More specifically, what is needed is a surgical clip and clip applier system particularly adapted for replacing a suture knot during endoscopic surgery which allows the surgical clip to exhibit adequate clamping force to function effectively.

A surgical clip particularly adapted for use with the present invention is a clip constructed of a memory shape material, such as is utilized in a preferred embodiment of commonly assigned U.S. patent application Ser. No. 09/120, 450. Memory shape materials may include compositions of nitenol, stainless steel, or any other composite of plastics, metals and/or resins. In order to more readily apply a surgical clip using endoscopic techniques, it is desired to provide an improved surgical clip applier.

For instance, there has been perceived a need for an improved clip applier capable of using self-closing surgical clips. Presently, prior art clip appliers such as the one described in U.S. Pat. No. 5,601,573 are constructed in such a manner that the clip applier has a jaw portion which obscures the surgical clips it applies. In fact, a window has been built into the upper jaw to compensate for the lack of visibility within these jaws. In performing a ligating procedure with this type of clip applier, the surgeon, or other operator, cannot easily see a surgical clip within the jaws of the clip applier to verify that the surgical clip has not become dislodged. If the window does not happen to be directly in a surgeon's line of sight, the surgeon will not be able to see whether a clip was loaded until the jaws are released from the closed position. If a clip was not loaded, the surgeon will need to grasp the tissue again and retry the clip applying process.

Another perceived problem with the design taught by the '573 patent is the direct exposure of the surgical clip to a tissue which is being ligated during the application process. During the application process, the clip is pushed distally into the jaws and onto the tissue. The first and second legs will contact the tissue as the clip enters the jaw as the clip is internal to the workings of the jaw, i.e., the jaw acts to pull the first leg away from the second leg using special rails, special tabs, and special shelves. Any imperfection in the legs of the clip, including the dimples taught by the '573 patent, may cause abrasion or damage to the tissue during the application process. Additionally the use of tabs with rails requires increased precision of tolerances, complexity, and cost in the manufacture of both the jaws of the clip as well as each individual surgical clips. If a clip is incorporated into the applicator which does not meet the tolerances required to fit within the special rails and shelves, the applicator will be jammed.

One other perceived problem with the design of the '573 patent is the initial unequal distribution of force along a tissue. Notice in FIG. 5D that when the clip applier applies the clip, the first and second legs form a V-shape. This V-shape of the leg members will result in an initial unequal distribution of force along the application tissue.

There is a perceived need to provide a surgical clip applicator which protects a tissue for a substantial portion of the application process.

There is another perceived need for a surgical clip applicator which provides improved visibility during application and which can utilize simply designed clips.

SUMMARY OF THE INVENTION

The present invention recognizes and addresses the foregoing disadvantages, and others, of prior art construction and methods.

Accordingly, it is an object of the present invention to provide a surgical clip applier for applying surgical clips. More particularly, it is an object of the present invention to provide an applicator having jaw mechanisms which provide an operator improved visibility of a particular clip during the ligating process. It is also an object of the present invention to provide a jaw mechanism which utilizes jaw faces internal to the clip.

A first advantage of a presently preferred embodiment is the use of separator ramps to separate two portions or legs of a self-closing surgical clip.

A second advantage of a presently preferred embodiment is the use of internal jaw faces which may protect tissue during the application process. Additionally, these internal jaw faces may be utilized by an operator, such as a surgeon, to position tissue to a desired location without applying a surgical clip.

A third advantage of the presently preferred embodiment includes the use of a first and second operating faces to further widen the gap between the legs of a self-closing surgical clip.

Another advantage of a presently preferred embodiment of the present invention is the external nature of the surgical clip's application relative to a first and second jaw face.

Still, another advantage of a presently preferred embodiment includes the use of application ramps. These ramps direct a surgical clip to a desired location during the application process.

Additional objects and advantages of the invention will be set forth in part in the following description, or may be obvious from the description or accompanying drawings, or may be learned through practice of the invention.

The accompanying drawings, which are incorporated in and constitute a part of the specification, illustrate several embodiments of the invention and together with the description, serve to explain the principles of the invention.

BRIEF DESCRIPTION OF THE DRAWINGS

FIG. 1 is a plan view of a preferred embodiment as viewed from the left side.

FIG. 2 is a plan view of the preferred embodiment of the present invention as viewed from the top.

FIG. 3 is a right side perspective view of the present invention as viewed at an angle.

FIG. 4 is a left side perspective view of the present invention viewed at an angle.

FIG. 5 is a plan view of the present invention as viewed from its rear.

FIG. 6 is a plan top view of a first jaw member with the interior shown in phantom.

FIG. 7 is a left side perspective view of the first jaw member as shown from an angle.

FIG. 8 is a left side perspective view of a second jaw member as shown from an angle.

Figure 10:
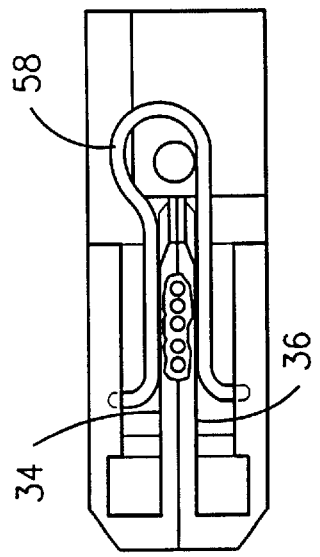
FIG. 10 is a left plan view of the present invention as shown with a surgical clip at a point during the installation procedure.

Repeat use of reference numerals in the present specification represent like, similar or analogous parts, features or elements of the present invention throughout several views.

DETAILED DESCRIPTION OF THE PREFERRED EMBODIMENTS

Reference will now be made in detail to the presently preferred embodiments of the invention, one or more examples of which are illustrated in the accompanying drawings. Each example is provided by way of explanation of the invention, not limitation of the invention. In fact, it will be apparent to those skilled in the art that modifications and variations can be made in the present invention without departing from the scope or spirit thereof. For instance, features illustrated or described as part of one embodiment may be used on another embodiment to yield still a further embodiment. Thus, it is intended that the present invention covers such modifications and variations as come within the scope of the appended claims and their equivalents.

The present invention is concerned with an improved surgical clip applier. This clip applier allows surgical clips to be positioned in a precise desired location by allowing the operator to visually see at least a portion of the surgical clip during a ligating procedure. Additionally, this invention allows for the positioning of a surgical clip on at least one outer face of a movable jaw. The jaw faces will contact a tissue prior to contact by a surgical clip. The operating faces may also impart an opening force to a self-closing clip. Furthermore, the preferred embodiment of the present invention provides visual access to at least a portion of a surgical clip to be applied to a particular location.

Accordingly, FIG. 1 depicts a presently preferred embodiment of a jaw portion 10 of a surgical clip applicator. The jaw portion 10 is comprised of a first jaw member 12 and a second jaw member 14. The first jaw member 12 is pivotally connected to the second jaw member 14 at a pivot, illustrated in FIG. 1 as a pin 16. The first jaw member 12 has a first connection portion 18 a first operating portion 22 as is illustrated in FIG. 2. At least one of the first jaw member 12 and the second jaw member 14 should be movable relative to a portion of the other jaw member. In the preferred embodiment, both the first jaw member 12 and the second jaw member 14 move relative to a fixed location about the pivot, however, one jaw member could be stationary while the other jaw member rotated about the pivot in an alternative embodiment.

The first jaw member 12 and the second jaw member 14, when pivoting about the pivot, have the first connecting portion 18 and the second connecting portion 20 rotate relative to the pivot. When the first jaw member 12 and the second jaw member 14 are pivoting relative to one another, the first connecting portion 18 and the second connecting portion 20 rotate in substantially parallel planes.

Figure 9:
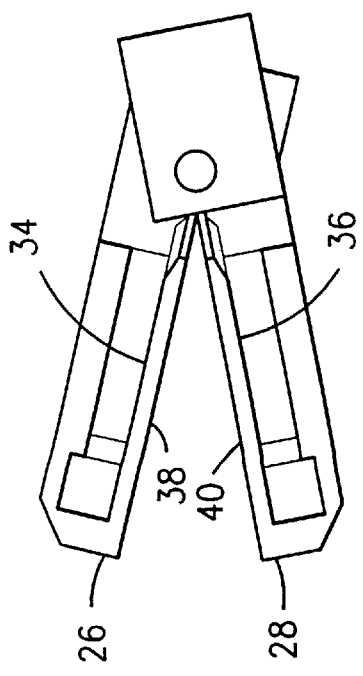
FIG. 9 is a plan view of the present invention as shown in an open position from the left side.

At the end of the first operating portion 22 of the first jaw member 12 is a first distal end 26. At the end of the second operating portion 24 of the second jaw member 14 is second distal end 28. FIGS. 1, 3, 4 and 5 show jaw portion 10 in a closed position. As the first jaw member 12 and second jaw member 14 rotate about the pivot relative to each other, the first distal end 26 and the second distal end 28 separate, as shown in FIG. 9.

Figure 11:
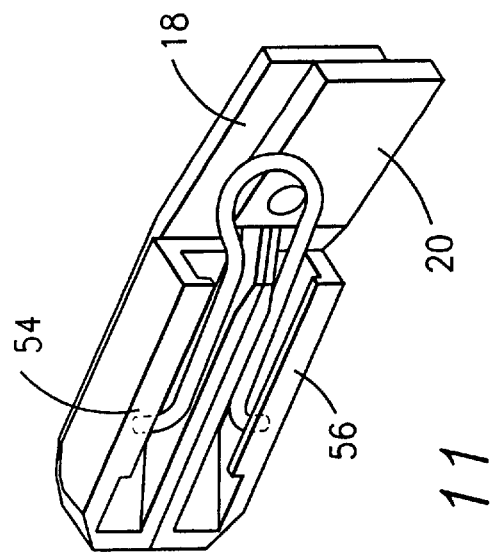
FIG. 11 is a the present invention illustrated in FIG. 4 with a surgical clip.

The first operating portion 22 has a first channel 30 illustrated in FIG. 7. The second operating portion 24 has a second channel 32 illustrated in FIG. 8. FIGS. 7 and 8 also show downwardly directed first jaw face 38 and upwardly directed second jaw face 40 of first and second jaw members 12,14. The first channel 30 and the second channel 32 provide surgical clip access areas. A surgical clip will traverse portions of the first and second channels 30,32 during the application process. The first and second retention lips 54,56 shown in FIG. 4, further assist in defining the first and second channels 30,32. FIG. 11 shows a clip partially installed within the first and second channels 30,32. The first and second retention lips 54,56 may be utilized to assist in retaining the clip within the first and second channels 30,32 until the clip contacts at least one of the application ramps.

Referring back to FIG. 1, located on the first operating portion 22 is a first operating face 34. The first operating face 34 is located substantially opposite to a portion of the first jaw face 38. The second operating portion 24 has a second operating face 36 opposite to a portion of the second jaw face 40. In the closed configuration shown in FIG. 1, at least a portion of the first jaw face 38 is in contact with a portion of the second jaw face 40.

A surgical clip design which has been found to be effectively utilized by this surgical clip applicator is one which is substantially U-shaped with the arcuate portion of the clip extending greater than one hundred-eighty degrees such that the distal ends of the clip are in closer proximity to each other than certain opposite portions of legs of the clip which are closer to the bend in the clip. The arcuate portion of the clip may also extend to have encompass an arc greater than five hundred forty degrees. An embodiment of this design would include a coil at the proximal portion of the surgical clip. Other designs of self-closing surgical clips may be effectively utilized with this type of surgical clip applier as well.

With the jaw portion 10 and the closed position as illustrated in FIGS. 1, 3, 4, and 5, a surgical clip may be advanced, at least partially, into the first channel 30 and the second channel 32. In order to advance a surgical clip into this position, the distal ends of a surgical clip are passed over the first and second separating ramps 42,44. This may best be visualized with reference to FIGS. 4, 5, 10, and 11. In some situations, it may be desirable for a surgical clip to contact only one of the first and second separating ramps 42,44, but in the preferred embodiment, both the first and second separating ramps 42,44 are utilized to initially separate the distal ends of a surgical clip. Alternatively, some embodiments of surgical clips may initially contact portions of the first and second operating faces 34,36 before contacting the first and second separating ramps 42,44, if the first and second separating ramps are contacted at all. First and second retention lips 54,56 may be utilized to assist in maintaining a clip in the first and second channels 30,32 until the clip reaches the first and second placement ramps 46,48. FIGS. 6 and 7 show views of the first leg member 12, illustrating a preferred shape of the first placement ramp 46.

Referring back to FIGS. 1, 3, 4 and 5, as a force is exerted on the surgical clip in a direction substantially towards the first and second distal ends 26,28 of the first and second operating portions 22, 24, the surgical clip will experience a separating force exerted by the first and second separating ramps 42, 44. Alternatively, the surgical clip may experience a separating force by either, or both of, the first or second operating faces 34, 36. Further still, the surgical clip may experience a separating force by some combination of the first and second operating faces 34,36 and the first and second separating ramps 42,44. The separating force will cause the distal ends of the surgical clip to separate. Typically, the force moving the clip toward distal ends 26,28 is applied by a more proximal clip which is ultimately pushed by a feed lug in a shaft connecting the clip applier to a handle.

In a preferred installment method, a tissue to be ligated is first grasped by the jaw portion 10 by rotating either, or both of, the first and second jaw members 12, 14 about the pivot such that the first and second distal ends 26, 28 are displaced from one another to a first position as is illustrated in FIG. 9. Referring back to FIGS. 1, 3, 4 and 5, the first and second jaw members 12, 14 are then rotated in the opposite direction about the pivot 16 such that the first and second distal ends 26 and 28 are brought closer to one another to a second position. The separation between the first and second distal ends 26,28 may be greater when the first and second jaw members 12,14 are in the first position than when the first and second jaw members 12,14 are in the second position. If a tissue grasped by the jaw portion 10 is sufficiently resilient, or if jaw faces 38,40 have an indentation to position tissue for ligation, it may be possible that the first and second distal ends 26, 28 of the first and second operating portions 22, 24 are substantially abutting one another, or are at least in close proximity to one another.

At this point in time, a self-closing surgical clip may have its legs separated by separating at least two portions of the self-closing surgical clip by forcing the clip distally over the first and/or second separating ramps 42, 44 and/or the first or second operating portions 22, 24 as shown in FIG. 10. If the first and second distal ends 26, 28 remain separated as a result of the tissue located between the first and second jaw faces 38, 40 when the jaw portion 10 is in the closed position, the first and second operating portions 22, 24 may assist in the separation of the self-closing surgical clip.

When the surgical clip is inserted into the jaw members 12,14 of the jaw portion 10, the interior surfaces of the leg members of the surgical clip 58 may contact the exterior surfaces of the first and second separating ramps 42,44. Similarly, the interior surfaces of the leg members of the surgical clip 58 will contact exterior surfaces of the first and second operating faces 34,36. The exterior surfaces of the first and second operating faces 34,36 are substantially opposite portions of the first and second jaw faces 38,40. The first and second jaw faces 38,40 have portions which may grasp and hold tissue. The first and second retention lips 54,56 may assist in maintaining the surgical clip 58 within the first and second channels 30,32 until the surgical clip is in position to install with a combination of the placement ramps 46,48,50,52.

FIG. 10 illustrates a first surgical clip 58 during the installation process. Interior surface portions of the legs of the first surgical clip 58 contact the first and second operating faces 34,36.

Referring back to FIGS. 1, 3, 4, and 5, the surgical clip may continue along the first and second channels 30, 32 until portions of the surgical clip contact the first and second placement ramps 46, 48 or rear placement ramps 50, 52 which will laterally displace the surgical clip 58 from the jaw portion 10. The first, second and/or rear placement ramps 46,48,50,52 will exert a lateral force on a surgical clip during the application process once the surgical clip reaches at least one of the placement ramps. This lateral force will result in lateral movement of the surgical clip. The surgical clip will then be displaced in a lateral direction a sufficient distance such that at least a portion of surgical clip will be displaced from the first or second operating faces 34,36.

At this point in time, the surgical clip will begin to self-close itself about the application tissue. In a presently preferred embodiment, the surgical clip will be displaced laterally so that the surgical clip is laterally installed in a plane substantially perpendicular to a plane of the surgical clip when the clip was in contact with portions of the first and second operating faces 34,36. Through the lateral installation procedure, the operator may be able to observe the surgical clip during a substantial portion of the installation procedure. The ability to see the clip is believed to be an advantage for the user.

The first and second jaw faces 38,40 may be utilized to dissect, scrape, manipulate, grasp tissue or other objects, hold, pinch, or locate objects independent of or in conjunction with the installation of surgical clips. Other tasks and functions may also be performed by the opening and closing of the jaws independent of clip application. The jaw portion 10 is also contemplated as being rotatable along an axis of rotation of a shaft (not shown) to which the jaw portion 10 is attached. Alternatively, the jaw portion 10 may rotate relative to the shaft to which it is attached. This may allow the jaw portion 10 to be rotated relative to a handle used by the operator so that the jaw members 12,14 are opened and closed in a direction desired by the operator while the handle may be located in a position chosen by the operator.

In an alternatively preferred embodiment, a surgical clip is inserted into the first and second channel 30, 32 by exerting a force on the surgical clip and pushing the two legs of a surgical clip on opposite separating ramps, the first and second separating ramps 42, 44. The surgical clip will then be slightly separated such that a first leg of the surgical clip is located along the first operating face 34 then a second leg of the surgical clip is located along the second operating face 36. The surgical clip should not be initially inserted so far that proximal ends of the distal clip reach the first or second placement ramps 46, 48.

An operator may then at least slightly open the jaw portion 10 by rotating the first jaw member 12 and the second jaw member 14 relative to the pivot 16 such that the first distal end 26 and the second distal end 28 are separated. Means for rotating the first jaw member 12 and/or the second jaw member 14 are known in the art. By the description of the rotation the first and second jaw members 12,14, it is intended to include all methods for having the jaw members 12,14 open and close. Other opening and closing methods may be utilized in some applications. Open jaw members are illustrated in FIG. 9. The separation of the first and second distal ends 26,28 will cause the distal ends of the surgical clip to become separated as the surgical clip is located external to the first and second jaw faces 38,40 when the surgical clip is installed prior to the opening of the jaw members.

The operator of the surgical clip apparatus may then choose a particular location to apply the surgical clip, if this location has not already been selected. The first and second jaw members 12,14 will then be placed on substantially opposite sides of the application location. The first and second jaw members 12,14 may then be rotated opposite to the direction which separated the first and second distal ends 26,28 of the first and second operating portions 22,24. The first and second distal ends 26,28 need not be substantially adjacent when applying clips to the application location, but in many applications, the operator may find that the pushing force required to apply a surgical clip to an application location may be reduced as the separation between the first and second distal ends 26,28 is reduced.

An operator may then continue to force the surgical clip towards the first and second distal ends 26, 28 of the first and second jaw members 12, 14. When a portion of the surgical clip comes into contact with the first and second placement ramps 46,48 as well as the first and second portions of the rear placement ramp 50, 52 the surgical clip begins to be displaced laterally in addition to its distal movement. In the preferred embodiment, the first, second and rear placement ramps 46, 48, 50 and 52 will cooperate with a surgical clip in order to displace the surgical clip from the jaw portion 10 of the surgical clip applier so that the surgical clip is installed in a plane substantially parallel to the plane of the first and second jaw members 12, 14.

An operator utilizing this jaw portion 10, may be able to see a surgical clip in portions of either, or both of, the first and second channels 30, 32. Further, the operator will be able to see portions of the surgical clip as the surgical clip contacts the first, second or rear placement ramps 46, 48, 50 and 52. Accordingly, the operator will be able to observe the precise placement of the surgical clip on the tissue to be ligated or occluded.

Some embodiments of the present invention may be constructed so that a surgical clip is applied upon a closure force of a fixed amount of the jaw portion 10. Other embodiments may incorporate means for the jaw to open and close without applying a surgical clip to a particular location. The operator would then be able to move tissue with the same jaws that would be utilized to attach a surgical clip at other locations. The mechanism of the surgical clip applicator which advances the surgical clips may be dependent or independent of the mechanism(s) which opens and/or closes the jaw portion 10. The jaw portion 10 may be connected to the applicator by operating means such that for every squeeze of the trigger, a clip is fired from the clip applier.

Alternative embodiments would include a double-action type of installation mechanism in which a trigger could be utilized to open and close the jaw portion 10 independent of the application of a clip. A second action, such as a separate trigger or the actuation of a single trigger to a second position would then result in the application of a clip.

Additionally, the methods of applying surgical clips utilizing the jaw portion 10 in a surgical clip applier as described above are contemplated by the present invention.

While preferred embodiments of the invention have been described above, it is to be understood that any and all equivalent realizations of the present invention are included within the scope and spirit thereof. Thus, the embodiments depicted are presented by way of example only and are not intended as limitations upon the present invention. While particular embodiments of the invention have been described and shown, it will be understood by those of ordinary skill in the art that the present invention is not limited thereto since many modifications can be made. Therefore, it is contemplated that any and all such embodiments are included in the present invention as may fall within the literal or equivalent scope of the appended claims.

What is claimed is:

1. An applicator having a jaw portion comprising:
   a first jaw member having a first operating portion, a first downwardly directed jaw face and a first distal end, said first operating portion having a first operating face opposite said first jaw face;
   a second jaw member having a second operating portion, a second upwardly directed jaw face, and a second distal end, said second operating portion having a second operating face opposite said second jaw face;
   wherein said second jaw member is movable relative to a portion of said first jaw member such that said first distal end and said second distal end are displaced a first distance from one another when in a first open position, and said first distal end and said second distal end are displaced a second distance from one another when in a second closed position said first distance being greater than said second distance; and wherein when a clip is inserted into the jaw members, said first and second operating faces separate the legs of said clip; and wherein the first jaw face and the second jaw face are in contact with tissue to be clipped when placed in the second closed position.

2. The applicator of claim 1 wherein the clip is a self-closing clip.

3. The applicator of claim 1 wherein the second jaw member is movable relative to a portion of the first jaw member about a pivot.

4. The applicator of claim 1 wherein the first operating portion further comprises a first placement ramp located along a portion of the first operating face.

5. The applicator of claim 4 wherein the second operating portion further comprises a second placement ramp located along a portion of the second operating face.

6. The applicator of claim 5 wherein each of the operating portions further comprises a rear placement ramp located proximal to at least one of the first or second placement ramps.

7. The applicator of claim 1 wherein the first operating portion further comprises a first separating ramp.

8. The applicator of claim 7 wherein the second operating portion further comprises a second separating ramp located at a proximal portion of the second operating face.

9. The applicator of claim 1 wherein the first and second jaw faces are substantially symmetrical.

10. The applicator of claim 1 wherein the first and second jaw members are substantially symmetrical.

11. The applicator of claim 6 wherein the first jaw member further comprises a first channel adjacent to the first placement ramp and first operating face, and said first channel is opposite the first jaw face.

12. The applicator of claim 11 wherein the first jaw member further comprises a first retention lip substantially parallel to a portion of the first operating face such that said retention lip, and the first placement ramp and the first operating face define an opening into the first channel.

13. The applicator of claim 12 wherein the first retention lip further comprises an interior surface portion which prevents lateral displacement of the clip out of one side of the first channel unless the clip is positioned at one of the first or second placement ramps.

14. The applicator of claim 11 wherein the second jaw further comprises a second channel adjacent to the second placement ramp and the second operating face.

15. The applicator of claim 14 wherein the second jaw member further comprises a second retention lip located along a portion of the second channel.

16. The applicator of claim 15 wherein the second retention lip prevents lateral displacement of the clip out of one side of the second channel unless said clip is positioned at one of the first or second placement ramps.

17. The applicator of claim 5 further comprising a rear placement ramp located proximal to at least one of the first and second placement ramps.

18. The applicator of claim 5 wherein at least one of the first and the second placement ramps are located toward the distal ends of their respective first and second jaw members.

19. The applicator of claim 5 wherein at least one of the first and second placement ramps displace the clip laterally from the jaw members.

20. The applicator of claim 6 wherein at least one of the first, second, and rear placement ramps displace the clip in a plane substantially perpendicular to a plane defined by the movement of the first jaw member relative to the second jaw member.

21. The applicator of claim 6 wherein at least one of the first, second, and rear placement ramps comprise a first plane which is at an angle between 1 and 89 degrees with a second plane which is defined by the movement of the first jaw member relative to the second jaw member.

22. A surgical applicator comprising:

a first jaw member having a distal end and a first downwardly directed jaw face opposite to a first operating portion;

a second jaw member having a distal end and a second upwardly directed jaw face opposite to a second operating portion;

wherein the second jaw member is movable relative to a portion of the first jaw member in a movement plane to bring the first and second jaw faces into contact with tissue between said first and second jaw faces; and said first and second operating portions receive a surgical clip and apply said clip to the tissue laterally from the jaw faces of the jaw members.

23. The surgical applicator of claim 22 wherein the first operating portion of the first jaw member further comprises a first operating face opposite to the first jaw face, a first placement ramp located towards a distal end of said fist operating face, a first channel located adjacent to said first operating face and said first placement ramp, and a first retention lip located substantially parallel to said first operating face;

said first placement ramp forming a first plane having an angle of between 1 and 89 degrees relative to the movement plane;

wherein the second operating portion further comprises a second operating face opposite to the second jaw face, a second placement ramp located towards a distal end of said second operating faces a second channel located adjacent to said second operating face and said second placement ramp, and a second retention lip located substantially parallel to said second operating face; and said second placement ramp forming a second plane having an angle of between 1 and 89 degrees relative to said movement plane.

24. A method of applying surgical clips with an applicator having a first jaw member having a first operating portion, a first downwardly directed jaw face and a first distal end, said first operating portion having a first channel and a first placement ramp located along a first operating face, said first operating face being substantially opposite said first jaw face;

a second jaw member having a second operating portion, a second upwardly directed jaw face and a second distal end, said second operating portion having a second channel and a second placement ramp located along a second operating face, said second operating face being substantially opposite said second jaw face;

a rear placement ramp located proximal to at least one of said first or second placement ramps; and wherein said second jaw member is movable relative to a portion of said first jaw member such that said first distal end and said second distal end are displaced a first distance from one another when in a first position, and said first distal end and said second distal end are displaced a second distance from one another when in a second position, said first distance being greater an said second distance, comprising the steps of:

(a) selecting the tissue to be ligated;

(b) moving said second jaw member relative to said first jaw member to said first position;

(c) placing said tissue between said jaw faces;

(d) moving said second jaw member relative to said first jaw member to said second position;

(e) advancing a clip having a first and a second leg into said jaw members such that the legs of said clip proceed in the first and second channels and said first and second operating faces assist in separating the legs of said clip;

(f) continuing advancing said clip until said clip contacts at least one of said first, second and rear placement ramps;

(g) advancing said clip along at least one of said first, second, and rear placement ramps until said clip is displaced to ligate said tissue.

25. A method of applying surgical clips with an applicator having a first jaw member having a first operating portion, a first jaw face and a first distal end, said first operating portion having a first channel and a first placement ramp located along a first operating face, said first operating face being substantially opposite said first jaw face;

a second jaw member having a second operating portion, a second jaw face and a second distal end, said second operating portion having a second channel and a second placement ramp located along a second operating face, said second operating face being substantially opposite said second jaw face;

a rear placement ramp located proximal to at least one of said first or second placement ramps; and wherein said second jaw member is movable relative to a portion of said first jaw member such that said first distal end and said second distal end are displaced a first distance from one another when in a first position, and said first distal end and said second distal end are displaced a second distance from one another when in a second position, said first distance being greater than said second distance, comprising the steps of:

(a) selecting the tissue to be ligated;

(b) advancing a clip having a first and a second leg into said jaw members such that the legs of said clip proceed in the first and second channels and said first and second operating faces assist in separating the legs of said clip;

(c) moving said second jaw member relative to said first jaw member to said first position;

(d) placing said tissue between said jaw faces;

(e) moving said second jaw member relative to said first jaw member to said second position;

(f) continuing advancing said clip until said clip contacts at least one of said first, second and rear placement ramps;

(g) advancing said clip along at least one of said first, second, and rear placement ramps until said clip is displaced to ligate said tissue.

* * * * *